(12) United States Patent
Kreindel

(10) Patent No.: US 8,652,130 B2
(45) Date of Patent: Feb. 18, 2014

(54) METHOD AND DEVICE FOR SOFT TISSUE ABLATION

(75) Inventor: Michael Kreindel, Richmond Hill (CA)

(73) Assignee: Invasix Ltd., Yokneam (IL)

( * ) Notice: Subject to any disclaimer, the term of this patent is extended or adjusted under 35 U.S.C. 154(b) by 730 days.

(21) Appl. No.: 12/858,463

(22) Filed: Aug. 18, 2010

(65) Prior Publication Data

US 2012/0046658 A1  Feb. 23, 2012

(51) Int. Cl.
*A61B 18/00* (2006.01)
*A61B 18/14* (2006.01)

(52) U.S. Cl.
USPC .................. 606/41; 606/32; 607/2; 607/115

(58) Field of Classification Search
USPC .................. 606/32–35, 41–45, 48–50; 607/2, 607/101–102, 115
See application file for complete search history.

(56) References Cited

U.S. PATENT DOCUMENTS

| | | | |
|---|---|---|---|
| 5,810,762 A | 9/1998 | Hofmann | |
| 6,326,177 B1 | 12/2001 | Schoenbach et al. | |
| 6,697,670 B2 * | 2/2004 | Chomenky et al. | 607/2 |
| 6,795,728 B2 | 9/2004 | Chornenky et al. | |
| 6,892,099 B2 | 5/2005 | Jaafar et al. | |
| 7,090,670 B2 | 8/2006 | Sink | |
| 2005/0171523 A1 * | 8/2005 | Rubinsky et al. | 606/34 |
| 2005/0261672 A1 * | 11/2005 | Deem et al. | 606/41 |
| 2007/0161982 A1 * | 7/2007 | Chornenky et al. | 606/43 |
| 2009/0254076 A1 * | 10/2009 | Altshuler et al. | 606/33 |
| 2009/0318916 A1 * | 12/2009 | Lischinsky et al. | 606/33 |
| 2010/0030211 A1 * | 2/2010 | Davalos et al. | 606/41 |
| 2010/0185194 A1 | 7/2010 | Kreindel | |
| 2010/0198216 A1 * | 8/2010 | Palanker | 606/41 |
| 2011/0015625 A1 * | 1/2011 | Adanny et al. | 606/33 |
| 2011/0238057 A1 * | 9/2011 | Moss et al. | 606/33 |

OTHER PUBLICATIONS

Hee-Kyu Lee, "Electrical Sterilization of Juice by Discharged HV, Impulse Wave Form," American Journal of Applied Sciences 2(10) : 2076-2078 (2006).

* cited by examiner

*Primary Examiner* — Michael Peffley
(74) *Attorney, Agent, or Firm* — Allen, Dyer, Doppelt, Milbrath & Gilchrist, P.A.

(57) ABSTRACT

A method and device for fractional skin treatment. The method includes the application of a HV pulse to the skin surface through an array of pin electrodes.

12 Claims, 4 Drawing Sheets

METHOD AND DEVICE FOR SOFT TISSUE ABLATION

FIELD OF THE INVENTION

The invention relates to methods and a device for non-thermal fractional skin ablation using high voltage (HV) electrical pulses.

BACKGROUND OF THE INVENTION

Skin rejuvenation is a one of the most popular cosmetic procedures.

Skin tissue consists of an outer epidermal layer overlying a dermal layer that is in contact with a layer of subcutaneous adipose tissue. Aging of the skin results in appearing such aging signs as wrinkle, rough skin texture and discoloration.

Fractional ablation of part of the skin during a few treatments results in skin resurfacing with minimal risk of skin damage. The fractional skin ablation results in localized heating and ablation of the skin area that is in exposed by applied energy. Ablation of the skin promotes skin resurfacing while untreated skin between the ablation dots promotes faster healing of the tissue. Damaged tissue is evacuated from the body by the lymphatic system.

The most popular method for fractional skin resurfacing is laser fractional ablation where laser energy focused onto the small spot of skin which is less than 1 mm and ablate it. $CO_2$, Erbium, Diode and Nd:Yag lasers in infrared spectrum range are used for this purpose. Laser beam is replaced with the scanner. The U.S. Pat. No. 7,090,670 describes array of laser beams used for paternal ablation of the skin.

The other method of fractional skin ablation is based on RF energy. Patent application US 2010/0185194 describes array of needles penetrating into the skin and creating fractional thermal ablation of the tissue.

The main limitation of the above described methods of thermal skin ablation is poorly controlled thermal zone around the ablated area. Heat transfer from the ablation zone may result in overlapping of thermal zones and potential skin scarring and dischromia especially for darker skin.

The alternative method of skin ablation is irreversible electroporation of the soft tissue that causes non-thermal damage of the cells.

U.S. Pat. No. 5,810,762 describes a device with support for treating target within the human body.

U.S. Pat. No. 6,795,728 describes a device with needles having an isolated shaft and a conductive tip which are inserted into the body to deliver HV into the fat tissue.

U.S. Pat. No. 6,892,099 describes a use of a long electrical pulse with duration above 10 microseconds for non-invasive treatment of tissue volume with fat. The main limitation of this invention is electrical shock associated with application of electrical voltage with pulsed duration longer than 10 microseconds. This strong effect on nerves inside the body is potentially dangerous and makes treatment not tolerable without general anesthesia.

U.S. Pat. No. 6,697,670 tries to overcome this limitation by combining HV pulse with a nerve stimulating signal but this effect is difficult to control.

The other invention described in the U.S. Pat. No. 6,326,177 describes a method of creating cell apoptosis using short pulses from 100 ps up to 1 microseconds. Using the short pulses allows the avoidance of nerve effect and makes the treatment potentially more friendly. From the other side, using short pulses require higher electric field strength above 10 kV/cm that creates electrical breakdown in the air. Such breakdown generates plasma that burns the skin and makes the use of high electric field pulses non-invasively not practical.

In spite of the attractiveness of electroporation technology, all of the above mentioned limitations resulted that there is no commercially available device in the market for irreversible electroporation.

The main limitations of electroporation are:
  The use of HV that may create arcing around electrode and damage the skin surface;
  Using long pulse or multiple pulses with single polarity may create risk of electrical shock; and
  In addition, generation of short pulses with amplitude of a few kilovolts has many technical challenges.

HV electrical pulses are also used for sterilization destroying bacteria. In article "Electrical Sterilization of Juice by Discharged HV Impulse Waveform", Hee-Kyu Lee, American Journal of Applied Sciences 2 (10): 2076-2078, 2006 has shown that survivability of the cells is a strong function of temperature and increase of temperature from 30° C. to 40° C. may provide the same survivability at twice the lower electric field strength.

The inventor herein believes that a non-invasive device for cosmetic treatment should satisfy to the following requirements:
  Pulse duration should not exceed 10 microseconds to avoid electrical shock and risk associated with it; and
  Pulse amplitude should be high enough to create irreversible damage to the cells but below breakdown threshold in the air over the skin surface.

SUMMARY OF THE INVENTION

The present invention provides a description of a method and a device for non-thermal ablation of a small portion of the skin using HV pulses. The electric field strength is increased locally by high curvature of the electrode attached to the skin surface. In addition, high curvature of the electrode limits the effected zone by about the radius of curvature. Divergence of electric field reduce electric field dramatically at larger distance. Use of a matrix of a small electrode allows simultaneous ablation of multiple zones in fractional manner. Use of a non-thermal method will increase comfort of the patient and decrease the risk of side effects.

Pulse duration and intensity of electrical current can be adjusted to provide gentle local skin heating simultaneously with electroporation. This will reduce the electroporation threshold.

In a first embodiment, parameters of HV pulses are delivered to the skin surface through the matrix of a needle applied to the skin.

In another embodiment, the HV pulses are delivered through the matrix of conductive dots on PCB.

In a third embodiment, parameters of HV pulse can be adjusted to generate thermal effect in the vicinity of the conductive pins in parallel with electroporation effect.

Skin can be preheated prior to applying HV pulses with a separate energy source to reduce the electroporation threshold.

The external heat source can be radio-frequency energy, laser, lamp, LED, microwave or preheated object.

The average electric field strength between electrodes should be in the range of 100 V/cm up to 5 kV/cm to avoid breakdown in the air. This is lower than the threshold of irreversible electroporation for cells at normal conditions with pulse duration below 10 microseconds. Pulse duration should be short enough to avoid electrical shocking. The preferable pulse duration is 1 microsecond to 10 microseconds. In order to increase efficiency of treatment a few pulses can be applied with delay long enough to avoid electrical shocking.

While average electric field strength between electrodes is below the 5 kV/cm the local electric field near the electrode surface can be in a few orders of magnitude higher if electrode curvature radius is much smaller than distance between electrodes.

The simplest model to estimate electrical field between small size pin and big electrode is spherical geometry.

Poison's equation in spherical geometry is $$\frac{\partial}{\partial r} r^2 \frac{\partial F}{\partial r} = 0$$

Where F is potential of electric field.
The solution of this equation is $$E(r) = \frac{V_0 r_0 R}{r^2 (R - r_0)}$$

Where
$V_0$—voltage between electrodes
R—radius of external electrodes (distance between pin and large electrode)
$r_0$—radius of pin The FIG. 1 shows electric field distribution between pin and large electrode. Where pin diameter is 200 microns, distance between electrodes is 2 mm and applied voltage is 1 kV. That provides average electric field strength of 5 kV/cm.

One can see that zone near the pin where electric field higher than 10 kV/cm is about 200 microns.

Thus, electroporation effect can be reached near the pin surface even at a very short pulse.

Thermal effect near the pin surface during electroporation treatment can be estimated using Joule's law:

$$T = \frac{t\sigma E^2}{C\rho}$$

Where
C—specific heat (3.6 J/g/K)
$\rho$—mass density (1 g/cm$^3$)
t—electrical pulse duration (100 ns)
$\sigma$—tissue conductivity (0.003 S/cm for wet skin and 0.001 S/cm for dry skin)

Calculated temperature increase in the skin and electrical field shown in FIG. 2.

One can see that in the zone of 20 microns the temperature increase will be about 10° K that will favor to epidermal electroporation.

The system comprises the following main components:
A hand piece applied to the skin surface and connected to the device;
A HV pulse generator is located in the hand piece and coupled directly to the electrodes to avoid high voltage pulse delivery through the long harness;
The system has a controller that controls hardware parameters and user interface including an LCD screen. The controller may have a microprocessor and dedicated software; and The hand piece comprises two electrodes. One of electrodes is a matrix of needles (pins) while the other electrode is planar and applied in the vicinity of the first electrode. The area of the planar electrode is large enough to provide good capacitive coupling even with dry skin.

Pin size should not exceed thickness of the skin to localize treatment effect in the dermis. The pin size should be in the range of 50 microns up to 3 mm Preferably, the pin size is in the range of 100 microns to 300 microns.

The distance between pins is larger than 300 microns.

This invention provides non-thermal ablation of skin in the zone less than 0.5 mm in vicinity of the each pin without damage to surrounding tissue.

This invention can be used for skin rejuvenation, treatment of wrinkles, scar treatment, pore reduction, cellulite treatment and skin tightening on the face and body.

To generally summarize the above, the invention is a system or device and method of use wherein the device is used for skin fractional treatment and comprises at least two electrodes configured to be coupled to a skin, wherein at least one electrode of said has a size smaller than a dermis thickness and is coupled to an area to be treated, and a HV generator connected to the electrodes, where the HV generator serves as means for delivering HV pulses with a duration not exceeding 10 microseconds and with an amplitude creating an irreversible electroporation effect in vicinity of at least one electrode which has a size smaller than the dermis.

At least one electrode comprises a matrix of a plurality of pins.

A desired HV pulse duration is preferably in the range of 1 microsecond to 10 microseconds. An average HV pulse amplitude is below 10 kV/cm. A heat source is provided to heat the skin prior to the application of HV pulses. At least one electrode comprises a matrix of pins and the other of the other of the at least two electrodes is a planar shaped electrode.

The method or process used for the fractional skin treatment comprising the steps of:
coupling at least two electrodes to the skin area to be treated wherein at least one electrode of has a size smaller than a dermis thickness; and applying a HV pulse with a duration preferably not exceeding 1 microsecond to 10 microseconds and with an amplitude creating an irreversible electroporation effect in vicinity of each pin of said at least one electrode.

The method further comprises the step of using a matrix of pins included in at least one electrode to cover a larger skin area with each pulse. The method further comprises the step of applying a HV pulse for creating an average electric field strength between said electrodes not exceeding 10 kV/cm. The method further comprises the step of heating the skin prior to the application of HV pulses.

Uses for the method and device include treatments related to skin rejuvenation, skin wrinkle treatment, cellulite reduction, skin pore size reduction, skin tightening, pigmented lesion treatment and Acne scar treatment.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
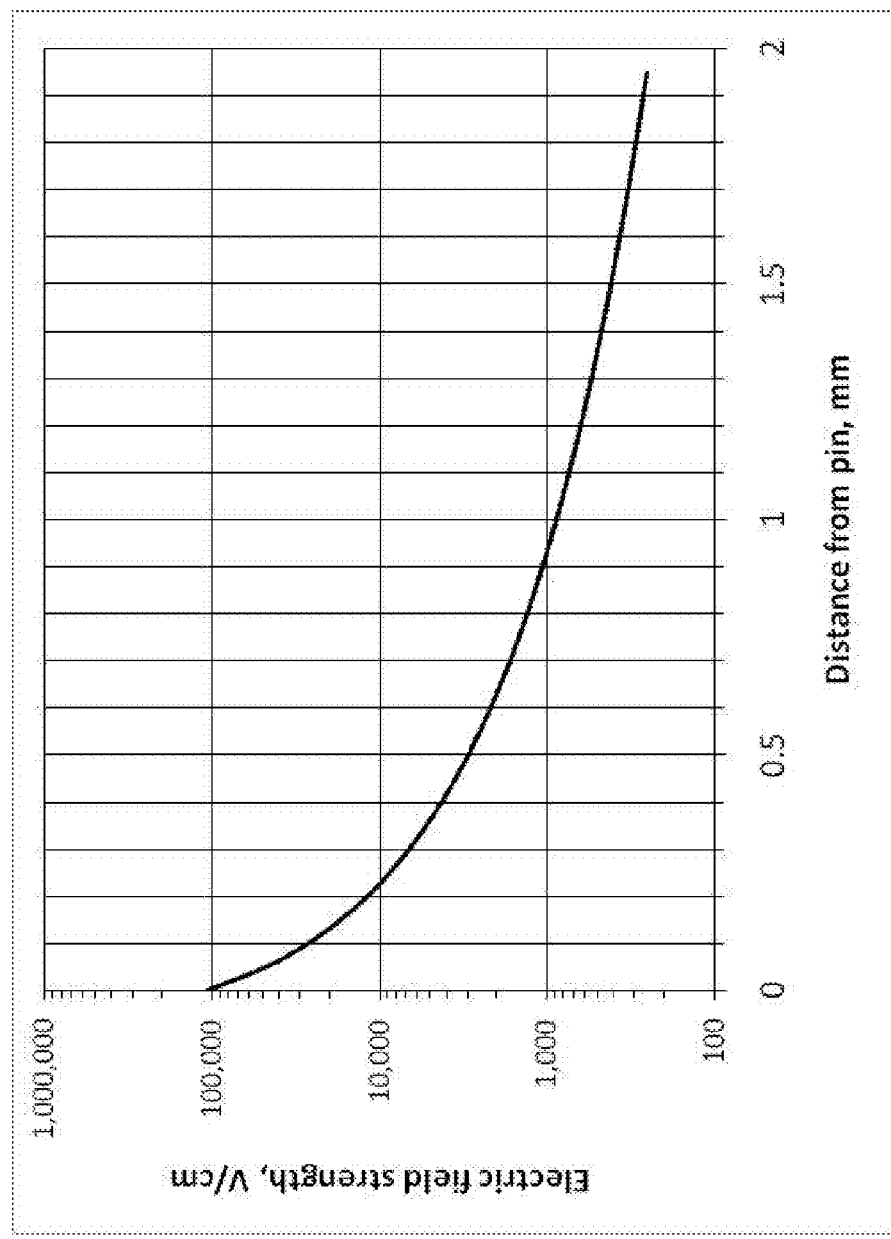
FIG. 1 shows electric field distribution between electrodes.
Figure 2:
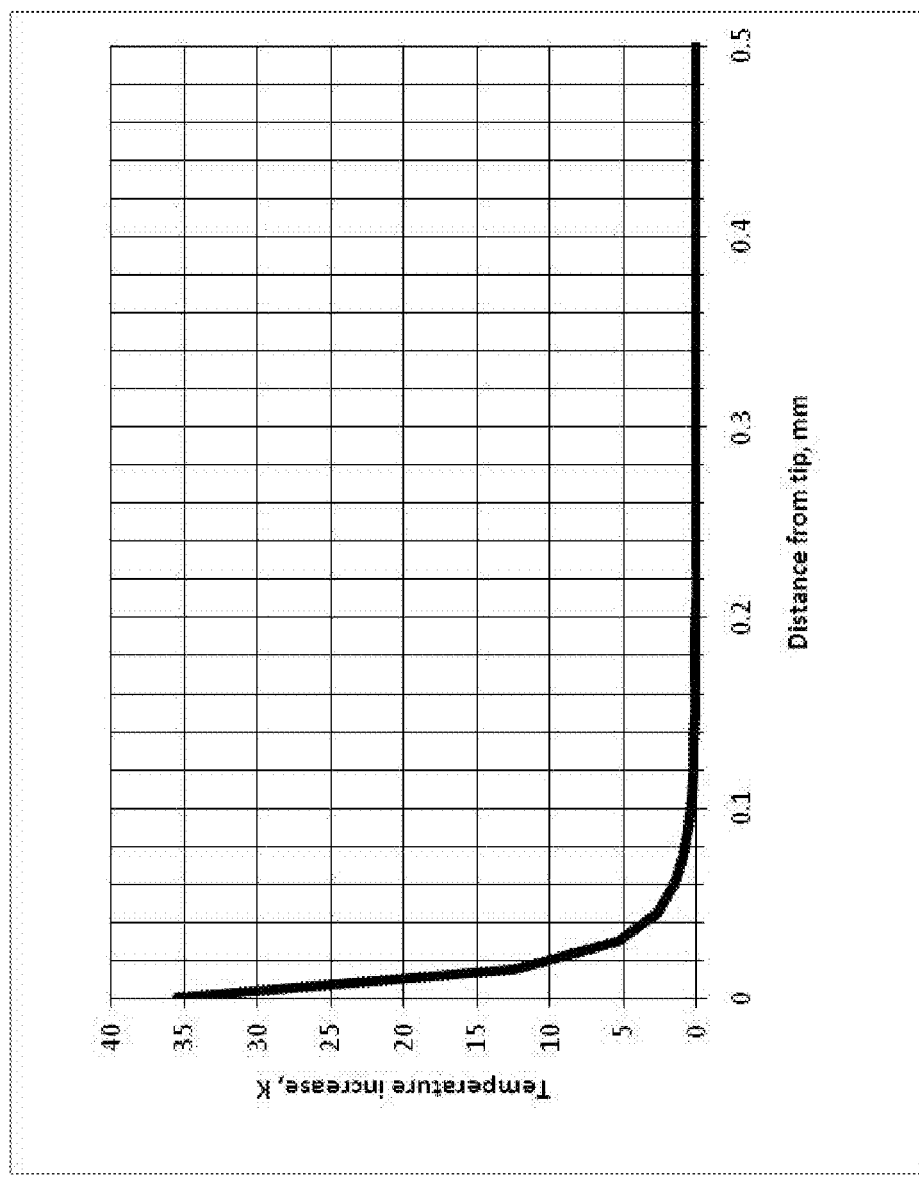
FIG. 2 shows heat generation by HV pulses between electrodes.
Figure 3:
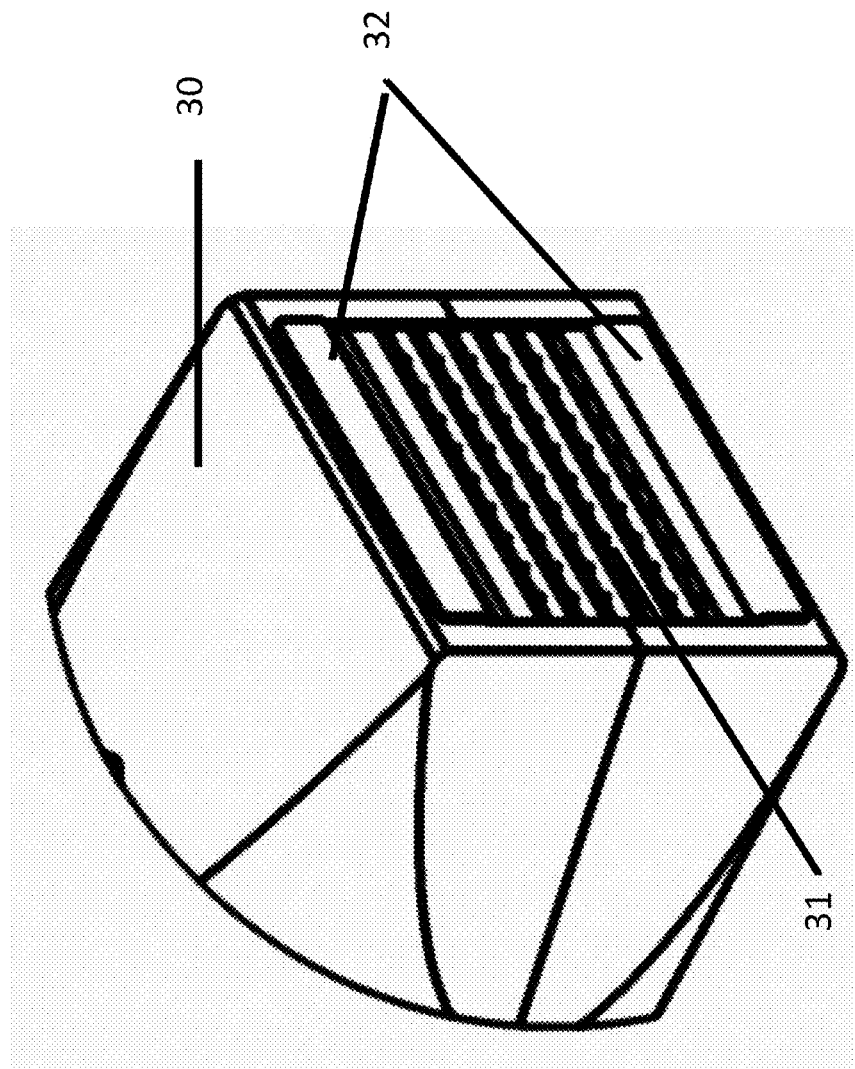
FIG. 3 shows a conceptual depiction of a hand piece design for fractional ablation of skin using electroporation.

Referring first to FIG. 3, a hand piece assembly conceptually shown in the figure comprises housing 30, a matrix of pin electrodes 31 and 2 flat electrodes 32 located at the side of the hand piece tip. Each tip has a diameter of 100 microns. The detailed description presents an example of one embodiment of the present invention with a design having 6 arrays of pins with 10 pins in each array. Pins 31 are protruded from hand piece by 200 microns to insure good contact between skin and pins during the treatment. All pins are connected electrically and high voltage is applied to the pins in a pulse manner. This voltage can be applied in a single pulse or in pulse burst. The return flat electrodes 32 are connected electrically to close current loop from the pin matrix. Contact area of the flat electrodes 32 is larger than total area of all pins.

Figure 4:
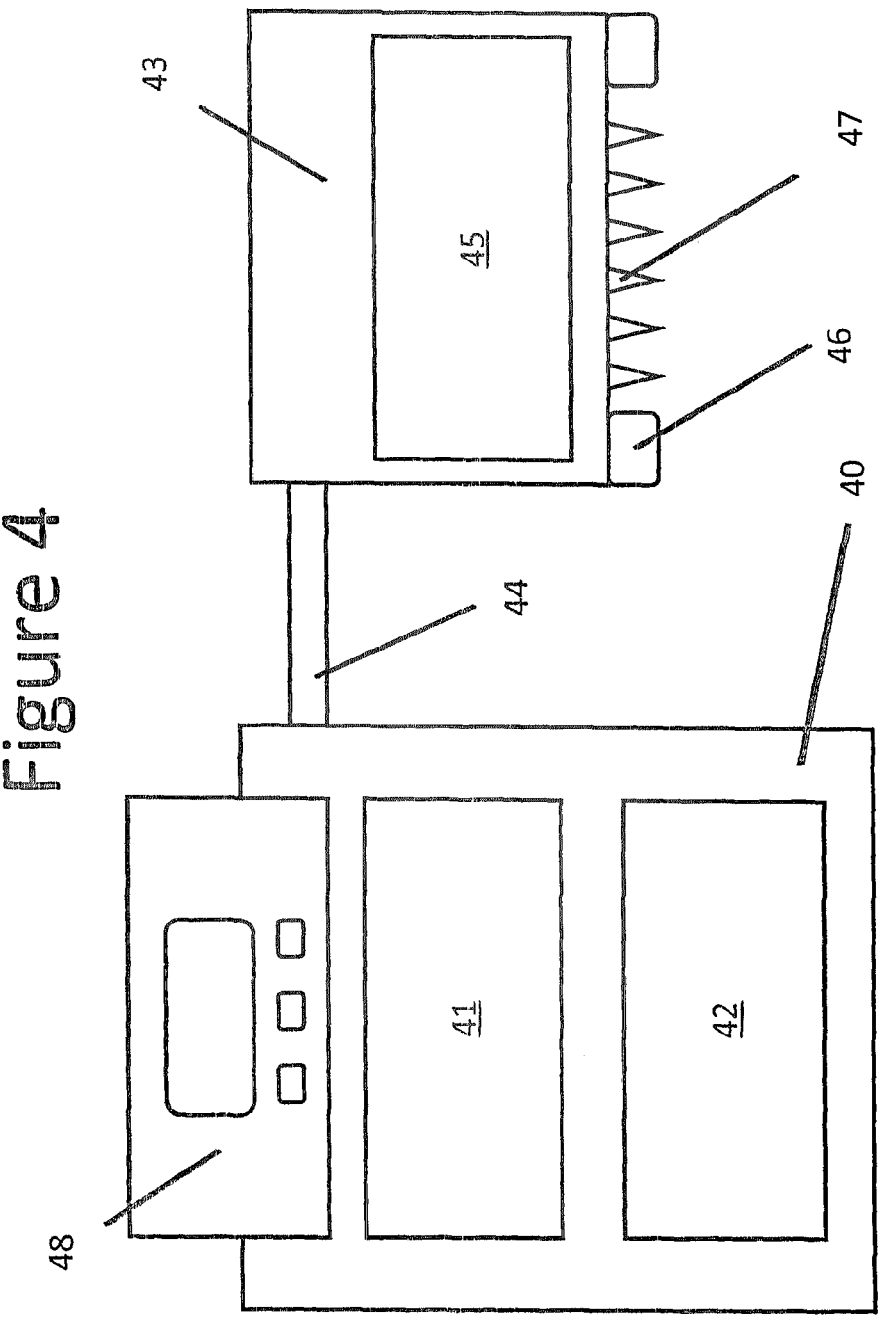
FIG. 4 is a conceptual schematic representation depicting an example of a device block diagram.

FIG. 4 shows a device unit 40 and hand piece 43 schematically. Unit 40 comprises a power supply 41 converting AC voltage to the stabilized DC voltage in the range of 12 VDC to 400 VDC. The controller module 42 gets power from power supply and controls all treatment parameters and provides interface with the user. Device unit 40 is connected to the hand piece 43 through the harness 44. HV pulse generator 45 is located in the hand piece 43 and connected directly to electrodes 46 and 47. HV power supply 45 gets power from the power supply 41 and HV pulse parameters from the controller 42. Controller 42 controls all or part of the following HV pulse parameters:

HV pulse amplitude;
HV pulse width;
Number of HV pulses; and
HV pulse repetition rate.

Controller 42 gets inputs from the operator through the interface 48 and adjusts output HV pulse parameters according to the inputs. User interface 48 includes LCD screen and buttons.

Using the system of the invention for skin rejuvenation, the following exemplary parameter values of HV pulses may be used:

HV pulse ampletude: 1-7 kV;
Pulse duration: 0.3-10 microseconds; and
Pulse repetition rate: 1 Hz to 1 kHz.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. A device for skin fractional treatment comprising:
   at least two electrodes configured to be coupled to a skin, wherein at least one electrode of said at least two electrodes includes a matrix of pins, each pin having a size smaller than a dermis thickness and for coupling to an area to be treated; and
   a HV generator connected to said at least two electrodes, said HV generator for delivering HV pulses with a duration not exceeding a desired predetermined time duration and with an amplitude creating an irreversible electroporation effect in the skin in vicinity of each of said pins without damaging the skin between the pins.

2. The device according to claim 1, wherein said predetermined time duration for said HV pulse duration is in the range of 1 microsecond to 10 microseconds.

3. The device according to claim 1, wherein an average HV pulse amplitude is below 10 kV/cm.

4. The device according to claim 1, further comprising:
   a heat source to heat the skin prior to the application of HV pulses.

5. The device according to claim 1, wherein the other of said at least two electrodes is a planar shaped electrode.

6. The device according to claim 1, further comprising a handpiece, the other of said at least two electrodes including a pair of flat electrodes arranged in a spaced apart parallel relationship on a face of the handpiece, the matrix of pins protruding from the handpiece between the pair of planar electrodes.

7. The device according to claim 6, wherein a contact area of the flat electrodes is larger than a total contact area of the matrix of pins.

8. A method of fractional skin treatment comprising the steps of:
   coupling at least two electrodes to the skin area to be treated wherein at least one electrode of said at least two electrodes includes a matrix of pins, each pin having a size smaller than a dermis thickness; and
   applying a HV pulse with a duration not exceeding a desired predetermined time duration and with an amplitude creating an irreversible electroporation effect in vicinity of each pin of said at least one electrode without damaging the skin between the pins.

9. The method according to claim 8, wherein said predetermined time duration for said HV pulse duration is in the range of 1 microsecond to 10 microseconds.

10. The method according to claim 8, further comprising the step of:
    applying a HV pulse for creating an average electric field strength between said electrodes not exceeding 10 kV/cm.

11. The method according to claim 8, further comprising the step of:
    heating the skin area to be treated prior to the application of HV pulses.

12. The method according to claim 8, wherein said method is used in any one of a treatment process selected from the group consisting of:
    skin rejuvenation, skin wrinkle treatment, cellulite reduction, skin pore size reduction, skin tightening, pigmented lesion treatment and acne scar treatment.

* * * * *